(12) United States Patent
Fujimoto et al.

(10) Patent No.: US 11,080,512 B2
(45) Date of Patent: Aug. 3, 2021

(54) INFORMATION PROCESSING DEVICE, INFORMATION PROCESSING METHOD, MEASUREMENT SYSTEM AND NON-TRANSITORY STORAGE MEDIUM

(71) Applicant: ARKRAY, Inc., Kyoto (JP)

(72) Inventors: Koji Fujimoto, Kyoto (JP); Shinya Nakajima, Kyoto (JP); Kenji Nakanishi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 5 days.

(21) Appl. No.: 16/653,073

(22) Filed: Oct. 15, 2019

(65) Prior Publication Data
US 2020/0134287 A1 Apr. 30, 2020

(30) Foreign Application Priority Data
Oct. 29, 2018 (JP) .............................. JP2018-202721

(51) Int. Cl.
*G06K 9/00* (2006.01)
*G06T 11/00* (2006.01)
(Continued)

(52) U.S. Cl.
CPC .......... *G06K 9/0014* (2013.01); *G01N 21/05* (2013.01); *G01N 21/17* (2013.01); *G01N 33/493* (2013.01);
(Continued)

(58) Field of Classification Search
CPC ............ G06K 9/0014; G06K 9/00147; G06K 9/00127; G01N 21/05; G01N 21/17;
(Continued)

(56) References Cited

U.S. PATENT DOCUMENTS 4,338,024 A * 7/1982 Bolz .................... G01N 15/147
356/23
4,393,466 A 7/1983 Deindoerfer et al.
(Continued)

FOREIGN PATENT DOCUMENTS

EP 2 083 375 A1 7/2009
EP 2 290 350 A1 3/2011
(Continued)

OTHER PUBLICATIONS

The extended European search report issued by the European Patent Office dated Apr. 1, 2020, which corresponds to EP19205499.7-1207 and is related to U.S. Appl. No. 16/653,073.

*Primary Examiner* — Kim Y Vu
*Assistant Examiner* — Molly Delaney
(74) *Attorney, Agent, or Firm* — Studebaker & Brackett PC

(57) ABSTRACT

An information processing device includes a categorizing section configured to extract a material component image identified as a material component from plural images obtained by imaging a sample fluid containing a plurality of types of material components and flowing through a flow cell, and to categorize the extracted material component image by predetermined category, a count derivation section configured to derive a count of the material component per standard visual field, or derive a count per unit liquid volume of the material component contained in the sample fluid, for each of the categories based on the number of material component images categorized by the categorizing section, and a generation section configured to generate an all-component image in which the material component images are arranged according to the counts that have been derived by the count derivation section for each of the categories.

14 Claims, 11 Drawing Sheets

(51) Int. Cl.
  *G01N 21/05* (2006.01)
  *G01N 21/17* (2006.01)
  *G01N 33/493* (2006.01)

(52) U.S. Cl.
  CPC ........ *G06K 9/00147* (2013.01); *G06T 11/001* (2013.01); *G01N 2021/1765* (2013.01)

(58) Field of Classification Search
  CPC ......... G01N 33/493; G01N 2021/1765; G01N 35/00871; G01N 21/84; G06T 11/001
  See application file for complete search history.

(56) References Cited

U.S. PATENT DOCUMENTS

| | | |
|---|---|---|
| 4,612,614 A | 9/1986 | Deindoerfer et al. |
| 2003/0170690 A1* | 9/2003 | Shatz ................... C07K 14/705 435/6.16 |
| 2008/0137937 A1* | 6/2008 | Athelogou ........... G06K 9/0014 382/133 |
| 2010/0317118 A1* | 12/2010 | Masujima ............... G01N 27/62 436/63 |
| 2011/0184254 A1* | 7/2011 | Grove .................. G01N 33/689 600/301 |
| 2014/0315237 A1* | 10/2014 | Masujima .............. G01N 33/48 435/29 |
| 2015/0063652 A1* | 3/2015 | Mangan ................ G06T 7/0012 382/110 |
| 2017/0186173 A1* | 6/2017 | Hakamada ............... G06T 7/194 |
| 2017/0213067 A1* | 7/2017 | Padmanabhan ...... G06K 9/0014 |
| 2017/0270666 A1* | 9/2017 | Barnes ...................... G06T 7/12 |
| 2018/0017480 A1* | 1/2018 | Fukuda ............. G01N 15/1459 |
| 2019/0271632 A1* | 9/2019 | Yang .................. G01N 33/5094 |
| 2019/0302093 A1* | 10/2019 | Hsu ........................ G01N 21/17 |
| 2019/0362491 A1* | 11/2019 | Rees .................... G06K 9/6274 |

FOREIGN PATENT DOCUMENTS

| | | |
|---|---|---|
| EP | 3 279 657 A1 | 2/2018 |
| JP | H03041783 B2 | 6/1991 |
| WO | 2014/145983 A1 | 9/2014 |

* cited by examiner

FIG.10

| | | | | | | | | | |
|---|---|---|---|---|---|---|---|---|---|
| | RBC | 23/uL | * | ✓ | WBCC | 1/HPF | ! | RBC | MOVE ALL |
| | WBC | 4/HPF | ! | ✓ | TRIP | 4/HPF | * | WBC | SWITCH DISPLAY |
| ✓ | NSE | 5/HPF | | ✓ | REEP | 5/HPF | * | NSE | VIEW ALL- |
| ✓ | SQEC | 2++ | | | WAXY | | | SQEC | COMPONENT IMAGE |
| | NHC | | | | CAOX | | | HYAL | |
| | BACT | 4+ | ↑ | | YST | | | NHC | 54A |
| | CRYS | | ↓ | | | | | BACT | |
| | YST | | | | | | | CRYS | |
| | HYST | | | ✓ | | | | YST | |
| | MUCS | | | ✓ | | | | HYST | |
| | SPRM | | | | | | | MUCS | |
| | UNCL | | | | | | | SPRM | |
| | DRBC | | | | | | | FAT | |
| | RBCC | | | | | | | TRCH | |
| | | | | | | | | PARA | |
| | | | | | | | | ART | |
| | | | | | | | | UNCL | |

54

FIG.11
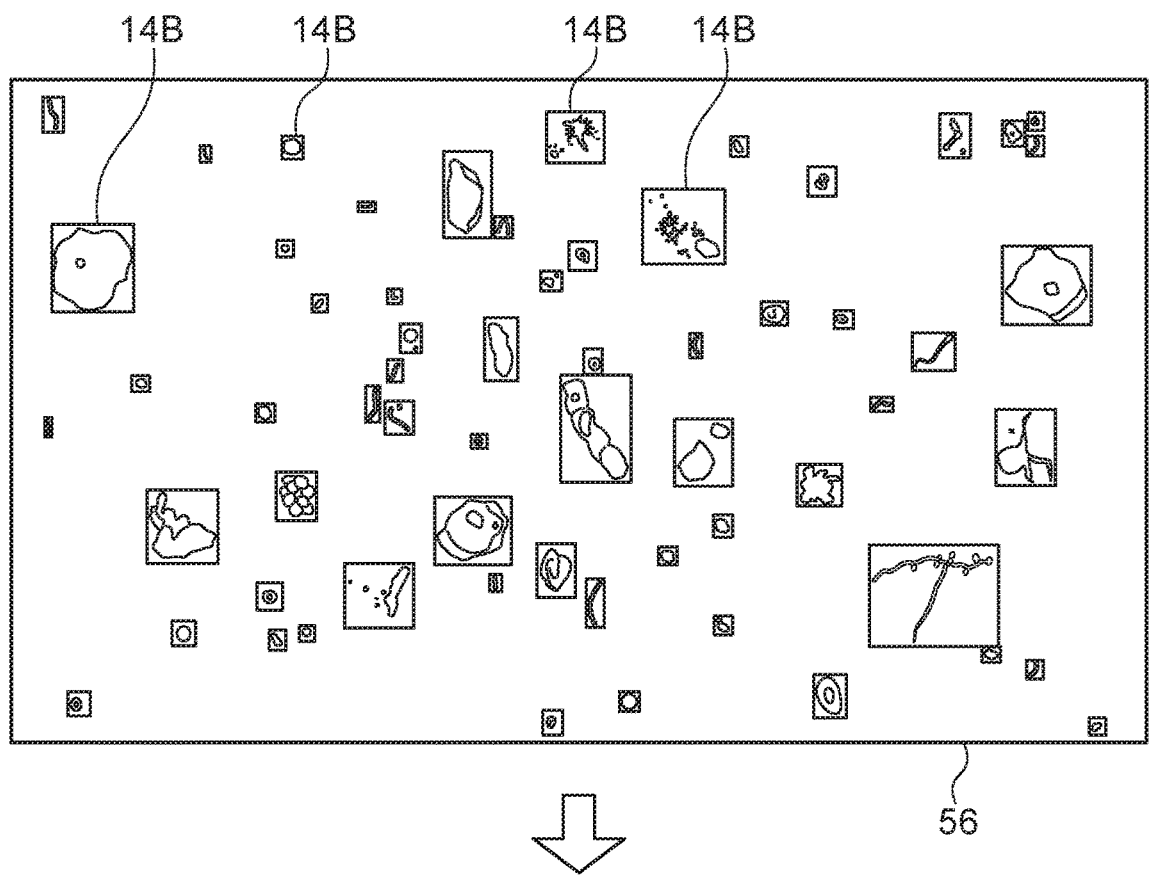
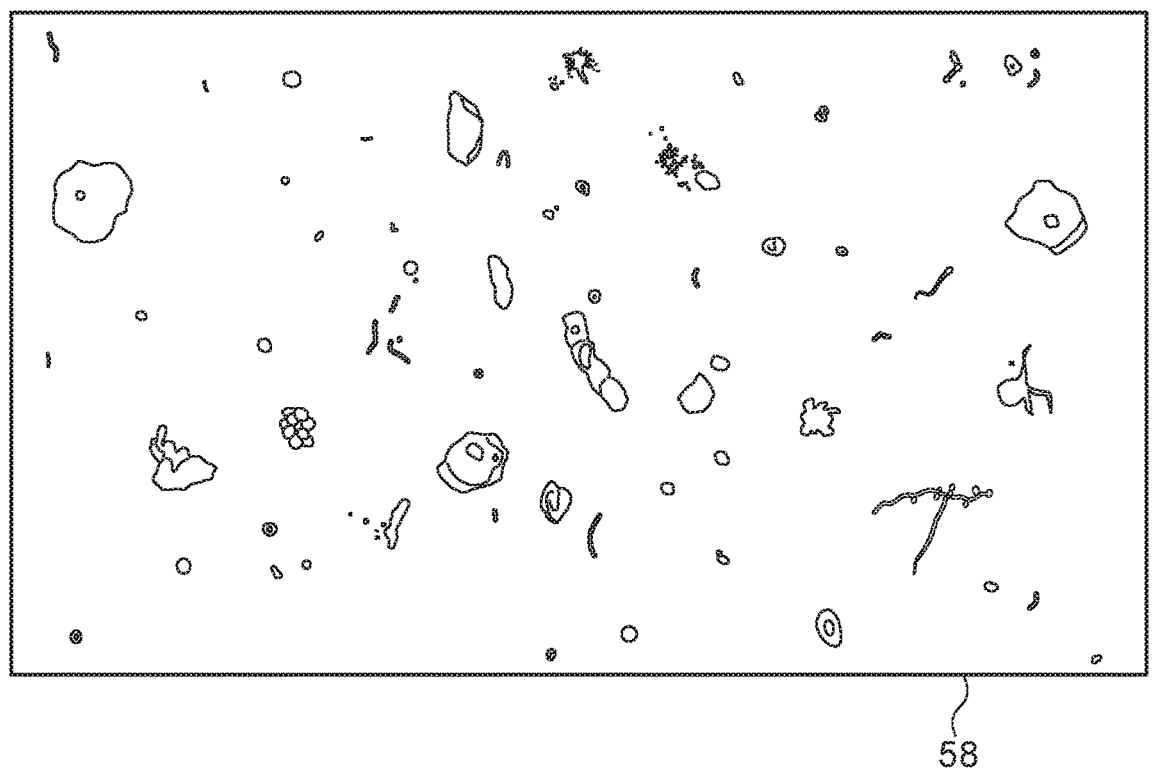

INFORMATION PROCESSING DEVICE, INFORMATION PROCESSING METHOD, MEASUREMENT SYSTEM AND NON-TRANSITORY STORAGE MEDIUM

CROSS-REFERENCE TO RELATED APPLICATION

This application is based on and claims priority under 35 USC 119 from Japanese Patent Application No. 2018-202721 filed on Oct. 29, 2018, the disclosure of which is incorporated by reference herein.

BACKGROUND

Technical Field

The present disclosure relates to an information processing device, an information processing method, a measurement system, and a non-transitory storage medium.

A urinary sediment examination is one example of a method in which material components contained in a sample solution are measured. A urinary sediment examination is an examination performed to investigate the amount and types of material components present in urine. In a urinary sediment examination, the content of each type of material component present in urine is investigated. In a urinary sediment examination, evaluation is performed based on measurements taken in a microscopic examination (standard method) using counts of material components present in a whole visual field (the range visible at any one time when viewed through a microscope). As an example of determination criteria, 0 to 4 red blood cells and 0 to 4 white blood cells in a whole visual field are determined to be normal. The whole visual field employed in evaluation varies according to the type of material components, and strong magnification (400×) or weak magnification (100×) may be employed. It is recommended to use 20 visual fields using an eyepiece lens having a magnification of 10×.

Progress is being made to automate such urinary sediment examinations (also referred to hereafter as "urinary material component examinations"). Broadly speaking, three methods are employed therefor: (1) observation and image capture of static samples using a microscope, (2) image capture using a flow method, and (3) scattergram analysis using a flow method.

For example, a method to display ultrafine particles is described in Japanese Patent Application Publication (JP-B) No. H03-41783. In this method a dilute biological liquid test sample containing ultrafine particles in a static state is not subjected to a physical concentration method such as centrifugal separation or the like, and instead the ultrafine particles are electronically concentrated. This method includes a step of distributing the liquid test sample over a wide area such that there is substantially no overlap between particles, and a step of forming plural still optical images of the liquid test sample to cover a plane of this area such that each of the still optical images represents a different location within this area. This method further includes a step of converting each of the still optical images into respective electronic images, and a step of combining images representing different particles from these electronic images to form a single composite electronic image. This method also includes a step of removing unnecessary image portions from the composite electronic image, or of processing the composite electronic image to extract useful image portions therefrom, and a step of displaying the processed composite electronic image as an image of the electronically concentrated ultrafine particles. Note that the method described in JP-B No. H03-41783 is technology relating to observation of a static sample using a microscope, as in method (1) above.

In image capture using a flow method as in method (2) above, images are captured of a test sample flowing through a flow cell, and material component images extracted from the captured images are categorized by material component type and examined. Image capture using a flow method does not allow the observation visual field to be moved or the magnification ratio to be changed while observing a sample, as is possible when observing a static sample through a microscope. Moreover, since the material component images extracted from the captured images are employed in analysis, the captured images themselves are not retained. Since an image of a static sample observed through a microscope includes various types of material components, there is accordingly a desire to view an image including plural material components even when image capture is performed using a flow method in order to enable the distribution of the material components and states of the material components to be observed at a glance.

SUMMARY

In consideration of the above circumstances, the present disclosure provides an information processing device, an information processing method, a measurement system, and a non-transitory storage medium capable of obtaining an image including plural material components such as that observed through a microscope, even in cases in which image capture is performed using a flow method.

An information processing device according to a first aspect of the present disclosure includes a categorizing section configured to extract a material component image identified as a material component, from plural images obtained by imaging a sample fluid containing plural types of material components and flowing through a flow cell, and to categorize the extracted material component image by predetermined category, a count derivation section configured to derive a count of the material component per standard visual field, or derive a count per unit liquid volume of the material component contained in the sample fluid, for each predetermined category based on a number of material component images categorized by the categorizing section, and a generation section configured to generate an all-component image in which plural of the material component images are arranged according to the counts that have been derived by the count derivation section for each predetermined category.

An information processing device according to a second aspect of the present disclosure is the first aspect, wherein the count derivation section is configured to use a predetermined calibration curve for each predetermined category to convert a number of the material component images into a resulting count per unit liquid volume of the sample fluid, and to use a predetermined correction coefficient for each visual field to derive a count per standard visual field from the resulting count per unit liquid volume.

An information processing device according to a third aspect of the present disclosure is the first aspect, wherein the generation section is configured to arrange the plural material component images so as not to overlap with each other.

An information processing device according to a fourth aspect of the present disclosure is the third aspect, wherein the generation section is configured to adjust a background color of each of the plural material component images to a uniform color tone.

An information processing device according to a fifth aspect of the present disclosure is the fourth aspect, wherein the color tone is determined by one out of an average value, a maximum value, or a minimum value of pixel values representing the background color in each of the plural material component images.

An information processing device according to a sixth aspect of the present disclosure is the first aspect, further including a control section configured to perform control so as to display the all-component image that has been generated by the generation section, wherein the control section is configured to perform control so as to selectively display only a specific material component image included in the all-component image.

An information processing device according to a seventh aspect of the present disclosure is the sixth aspect, wherein the control section is further configured to perform control so as not display any material component image selected among the plurality material component images included in the all-component image, or to not display a number of images exceeding an upper limit value for material component images selected.

An information processing device according to an eighth aspect of the present disclosure is the first aspect, further including a storage section storing categorized material component images and a setting section configured to set an upper limit for each of the categories for a number of the material component images, among the material component images that have been categorized by the categorizing section, to be stored in the storage section.

An information processing device according to a ninth aspect of the present disclosure is the eighth aspect, wherein the generation section is configured to duplicate material component images stored in the storage section in a case in which a number of material component images for each predetermined category to be arranged as part of the all-component image exceeds the upper limit, so as to acquire material component images for the amount by which the upper limit is exceeded.

An information processing method according to a tenth aspect of the present disclosure includes extracting a material component image identified as a material component from plural images obtained by imaging a sample fluid containing plural types of material components and flowing through a flow cell, and categorizing the extracted material component image by predetermined category, deriving a count of the material component per standard visual field, or deriving a count per unit liquid volume of the material component contained in the sample fluid, for each predetermined category based on a number of categorized material component images, and generating an all-component image in which plural of the material component images are arranged according to the counts that have been derived for each predetermined category.

A measurement system according to an eleventh aspect of the present disclosure includes a flow cell configured to allow a sheath fluid and a sample fluid that contains plural types of material components to flow through, an imaging section configured to image the sample fluid flowing through the flow cell, and the information processing device of the first aspect input with plural images obtained by imaging with the imaging section.

A non-transitory storage medium according to a twelfth aspect of the present disclosure stores a program for causing a computer to execute processing. The processing includes extracting a material component image identified as a material component from plural images obtained by imaging a sample fluid containing plural types of material components and flowing through a flow cell, and categorizing the extracted material component image by predetermined category, deriving a count of the material component per standard visual field, or deriving a count per unit liquid volume of the material component contained in the sample fluid, for each predetermined category based on a number of categorized material component images, and generating an all-component image in which plural of the material component images are arranged according to the counts that have been derived for each predetermined category.

As described above, an image including plural material components such as that observed through a microscope may be obtained, even in cases in which image capture is performed using a flow method.

BRIEF DESCRIPTION OF THE DRAWINGS

Exemplary embodiments of the present invention will be described in detail based on the following figures, wherein:

FIG. 10 is a face-on view illustrating an example of a measurement result screen according to an exemplary embodiment, and FIG. 11 is a diagram to explain a process for generating an all-component image according to an exemplary embodiment.

DETAILED DESCRIPTION

Detailed explanation follows regarding an example of an exemplary embodiment of the present disclosure, with reference to the drawings.

Figure 1:
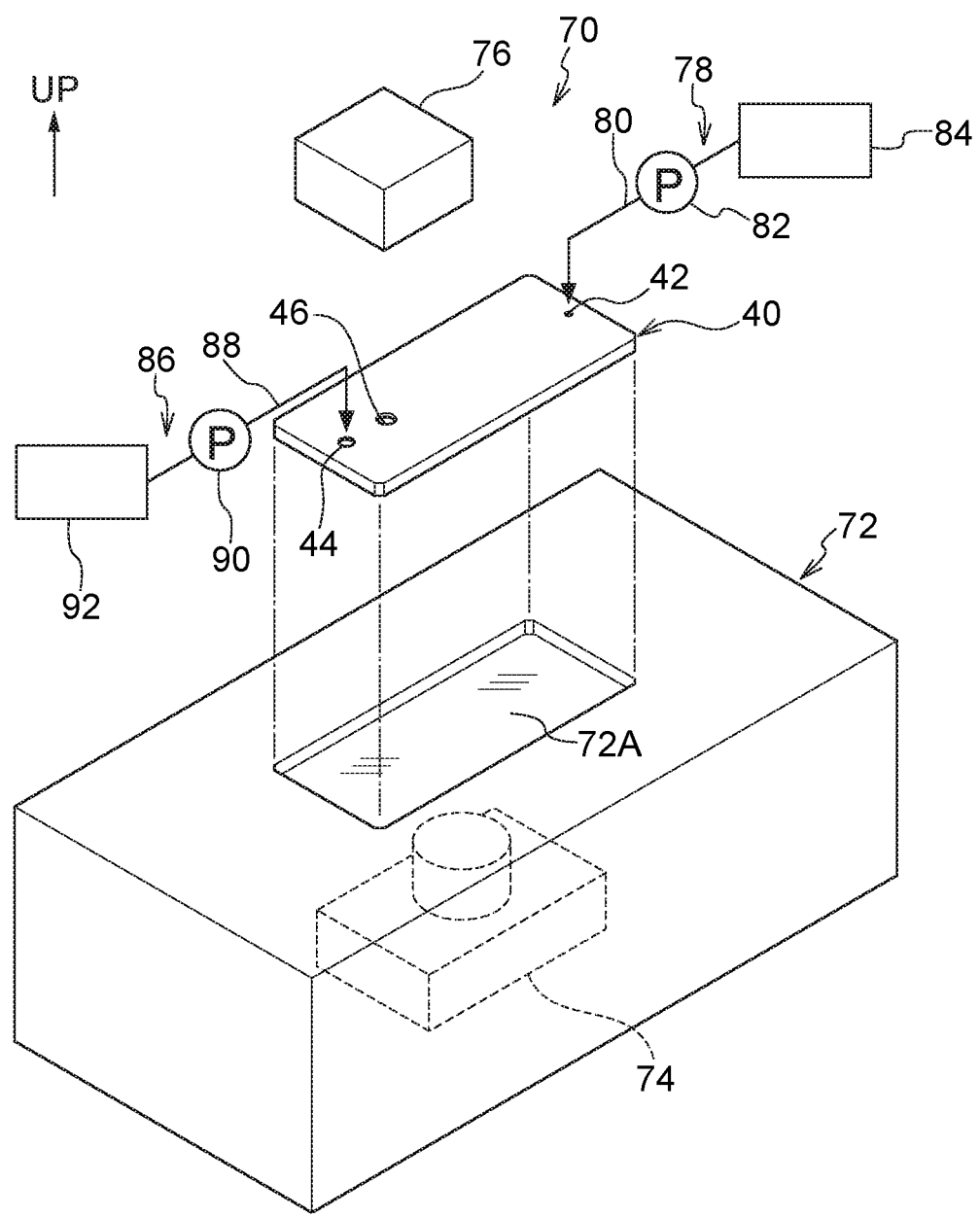
FIG. 1 is a perspective view illustrating part of a configuration of a measurement system according to an exemplary embodiment.

FIG. 1 is a perspective view illustrating part of a configuration of a measurement system 70 according to the present exemplary embodiment.

As illustrated in FIG. 1, the measurement system 70 according to the present exemplary embodiment includes a flow cell 40, casing 72, a camera 74, and a light source 76.

Note that the arrow UP in FIG. 1 indicates upward in a vertical direction of the measurement system 70.

The flow cell 40 according to the present exemplary embodiment is, for example, applicable to urinary material component examinations (urinary sediment examinations) in which a urine sample serving as an example of a sample fluid is introduced together with a sheath fluid in order to capture images of material components in the urine sample using the camera 74 and to perform various analyses based on the shapes etc. of the material components in the captured image. The camera 74 is an example of an imaging section. Although explanation follows regarding an example of the present exemplary embodiment in which a urine sample is not in a concentrated state, a concentrated sample may also be employed therefor. Plural types of material components (solid components) are contained in the urine sample. Examples of types of material components include red blood cells, white blood cells, epithelial cells, casts, bacteria, and the like. Note that although in the present exemplary embodiment a case is described in which a urine sample serving as an example of a sample fluid is used to perform a urinary material component examination, blood, cells, bodily fluids, or the like may also be employed for material component examination.

The measurement system 70 includes the casing 72 to place the flow cell 40 in. A recess 72A for inserting the flow cell 40 into is formed in the casing 72. A position of the casing 72 that includes where the recess 72A is provided is formed by a transparent member (for example glass). The camera 74 is provided inside the casing 72 at a position facing toward the flow cell 40. The light source 76 is provided at the upper side of the casing 72, at a position facing toward the camera 74 across the flow cell 40. The camera 74 is disposed at a position that enables the sample fluid flowing through the flow cell 40 to be imaged.

The measurement system 70 includes a first supply device 78 to supply the sample fluid into a sample intake port 42 of a sample flow path (not illustrated in the drawings) in the flow cell 40. The first supply device 78 includes a supply tube 80 having one end connected to the sample intake port 42, a pump 82 provided partway along the supply tube 80, and a sample storage section 84 for storing the sample fluid in that is connected to the other end of the supply tube 80.

The measurement system 70 includes a second supply device 86 to supply the sheath fluid into a sheath intake port 44 of a sheath flow path (not illustrated in the drawings) in the flow cell 40. The second supply device 86 includes a supply tube 88 having one end connected to the sheath intake port 44, a pump 90 provided partway along the supply tube 88, and a tank 92 for storing the sheath fluid in that is connected to the other end of the supply tube 88.

A discharge port 46 is also provided to the flow cell 40 between the sample intake port 42 and the sheath intake port 44. One end of a discharge tube (not illustrated in the drawings) is connected to the sheath intake port 46, and the other end of the discharge tube is connected to a waste tank (not illustrated in the drawings). The flow cell 40 includes a merging section (not illustrated in the drawings) to merge the sample introduced through the sample intake port 42 with the sheath fluid introduced through the sheath intake port 44, and the merged fluid flows through a flow path. A tapered section is formed in the flow path where the height of the flow path gradually decreases. The sample therefore does not disperse in the sheath fluid even after the sample has merged with the sheath fluid, and instead the flow is localized to a flattened shape. The material components in the localized sample fluid are imaged by the camera 74.

Figure 2:
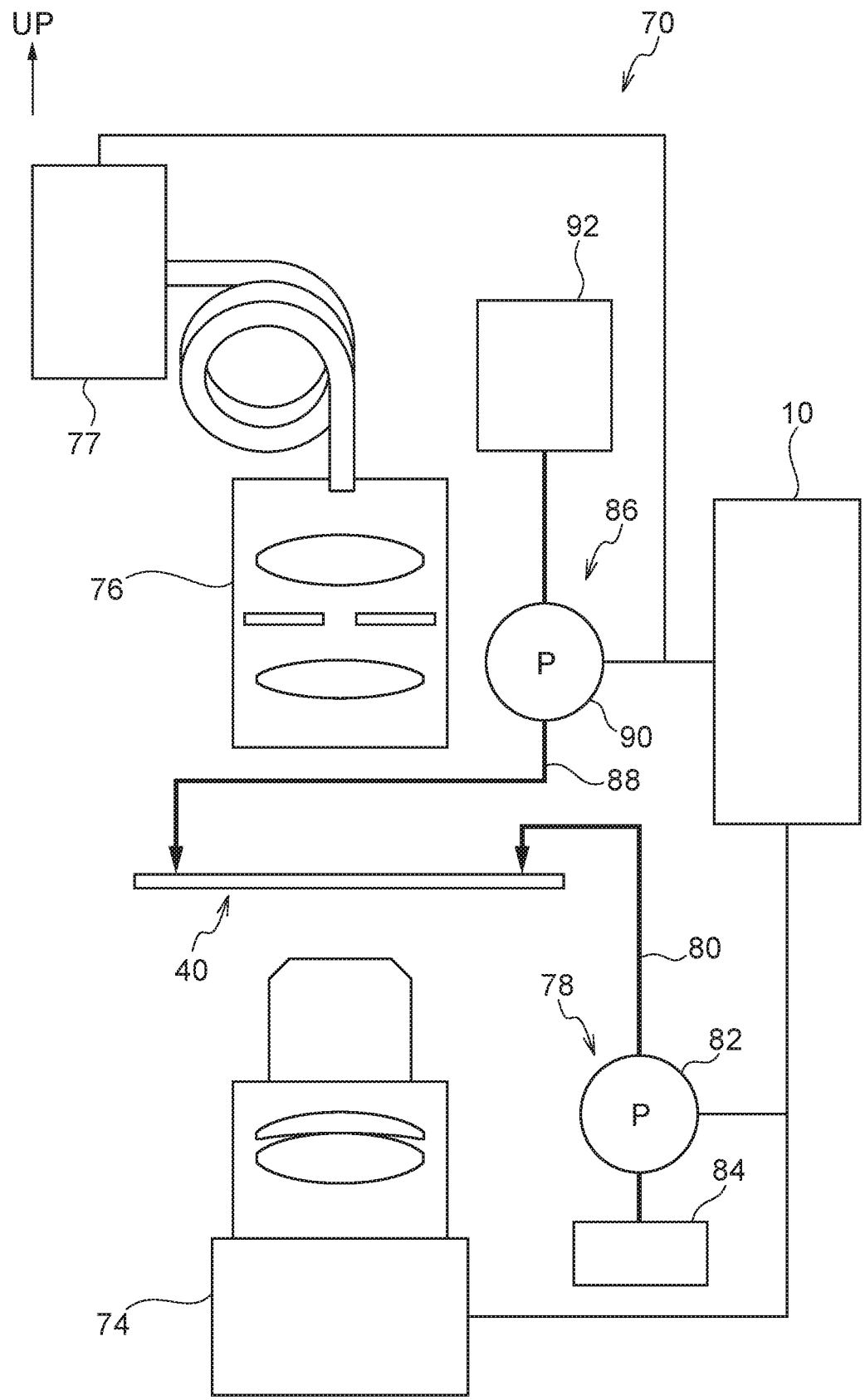
FIG. 2 is a schematic diagram illustrating an example of configuration of a measurement system according to an exemplary embodiment.

FIG. 2 is a schematic diagram illustrating an example of a configuration of the measurement system 70 according to the present exemplary embodiment.

As illustrated in FIG. 2, the measurement system 70 according to the present exemplary embodiment includes an information processing device 10. Note that the arrow UP in FIG. 2 indicates upward in the vertical direction of the measurement system 70, similarly to in FIG. 1.

The information processing device 10 includes the functionality of a control device to control the respective operations of the camera 74, a light source actuation section 77 electrically connected to the light source 76, the pump 82, and the pump 90. The information processing device 10 applies a pulse signal to the light source actuation section 77 so as to cause the light source 76 to emit light at a predetermined interval. The information processing device 10 drives the pump 82 to control the flow rate of the sample fluid, and drives the pump 90 to control the flow rate of the sheath fluid.

Figure 3:
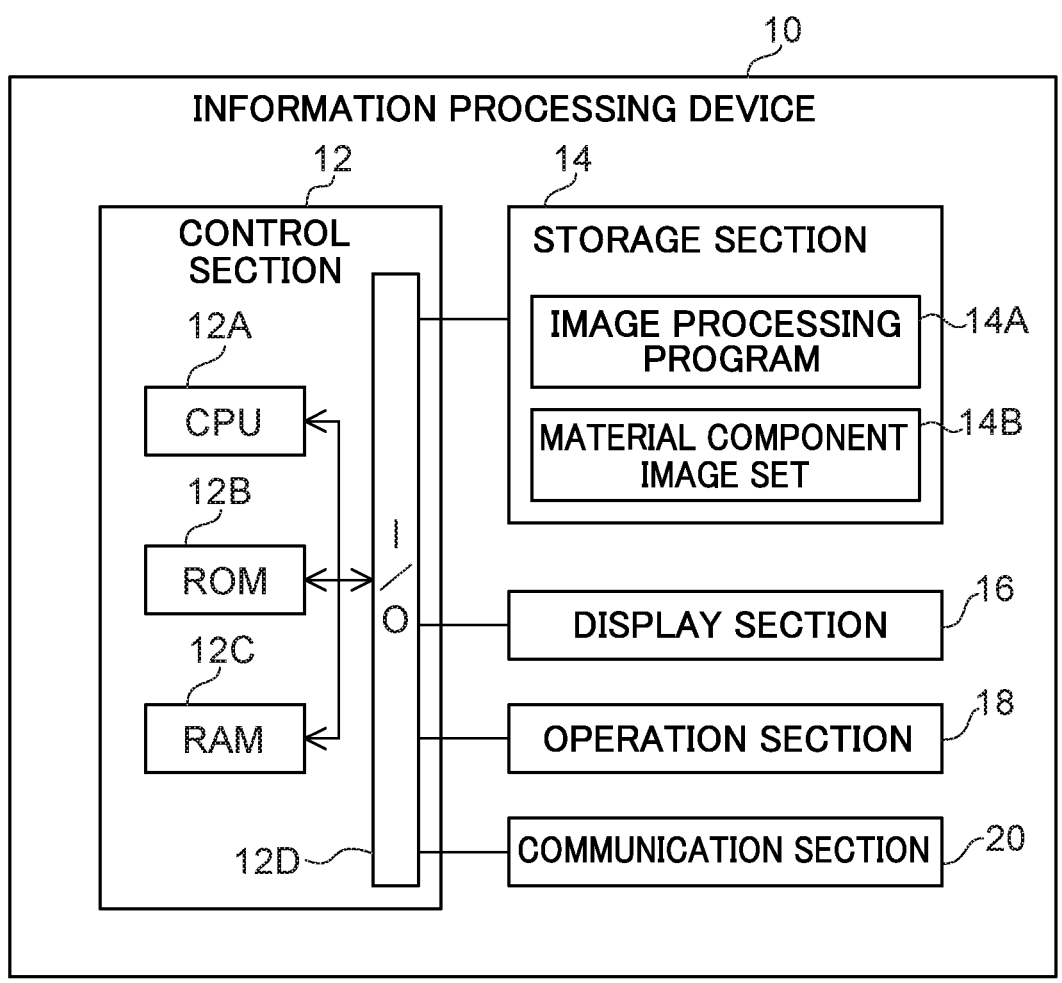
FIG. 3 is a block diagram illustrating an example of an electrical configuration of an information processing device according to an exemplary embodiment.

FIG. 3 is a block diagram illustrating an example of an electrical configuration of the information processing device 10 according to the present exemplary embodiment.

As illustrated in FIG. 3, the information processing device 10 according to the present exemplary embodiment includes a control section 12, a storage section 14, a display section 16, an operation section 18, and a communication section 20.

For example, a generic computer such as a personal computer (PC) is employed as the information processing device 10 according to the present exemplary embodiment. Note that a mobile computer such as a smartphone, tablet, or the like may also be employed as the information processing device 10. The information processing device 10 may also be split between plural units. For example, the information processing device 10 may be configured so as to include a unit for controlling a measurement system composed of the camera 74, the light source 76, the pump 82, the pump 90 etc., and to include a unit to perform processing and analysis on images captured by the camera 74. The information processing device 10 may be an external device connected to the measurement system 70.

The control section 12 includes a central processing unit (CPU) 12A, read only memory (ROM) 12B, random access memory (RAM) 12C, and an input/output interface (I/O) 12D. These sections are connected together through a bus.

Each of the functional sections including the storage section 14, the display section 16, the operation section 18, and the communication section 20 are connected to the I/O 12D. These functional sections are capable of communicating with the CPU 12A through the I/O 12D.

The control section 12 may be configured as a sub-control section to control the operation of parts of the information processing device 10, or may be configured as part of a main control section to control overall operation of the information processing device 10. For example, large scale integrated (LSI) circuits or integrated circuit (IC) chip sets are employed for some or all of the respective blocks of the control section 12. A separate circuit may be employed for each block, or circuits integrating together some or all of the blocks may be employed. The respective blocks may be provided so as to be integrated together, or some of the blocks may be provided separately. Alternatively, parts of the respective blocks may be provided separately. Integration of the control section 12 is not limited to integration employing LSIs, and dedicated circuits or generic processors may also be employed therefor.

Examples of the storage section 14 include a hard disk drive (HDD), a solid state drive (SSD), a flash memory, or the like. An image processing program 14A to perform processing for all-component image generation according to the present exemplary embodiment is stored in the storage section 14. Note that the image processing program 14A may alternatively be stored in the ROM 12B. The storage section 14 is also stored with a material component image set 14B for use in the all-component image generation processing. Note that the storage section 14 may have external memory attached that is expanded later.

The image processing program 14A may, for example, be pre-installed in the information processing device 10. The image processing program 14A may be stored on a non-volatile storage medium, or may be implemented by being distributed via a network and installed or uploaded to the information processing device 10 as appropriate. Note that examples of non-volatile storage media include compact disc read only memory (CD-ROM), a magneto-optical disc, an HDD, digital versatile disc read only memory (DVD-ROM), flash memory, a memory card, and so on.

For example, a liquid crystal display (LCD) or an organic electro luminescence (EL) display may be employed as the display section 16. The display section 16 may include an integral touch panel. A device for operation input, such as a keyboard or a mouse, may be provided to the operation section 18. The display section 16 and the operation section 18 receive various instructions from a user of the information processing device 10. The display section 16 displays various information, such as the result of processing executed in response to an instruction received from the user and notifications relating to processing.

The communication section 20 is connected to a network such as the internet, a local area network (LAN), or a wide area network (WAN), and is capable of communicating over the network with external devices such as an image forming device or another PC.

When performing image capture using a flow method employing the flow cell 40 as described above, images of the sample fluid flowing through the flow cell 40 are captured, and anything identified as a material component is extracted from the captured images. These extracted images of material components are categorized by material component type, and examined. This accordingly means that an all-component image resembling an observation through a microscope is not obtainable. There is accordingly a desire to view an all-component image including plural material components even when image capture is performed using a flow method, in order to enable the distribution of the material components and states of the plural material components to be observed at a glance in such an all-component image.

Figure 4:
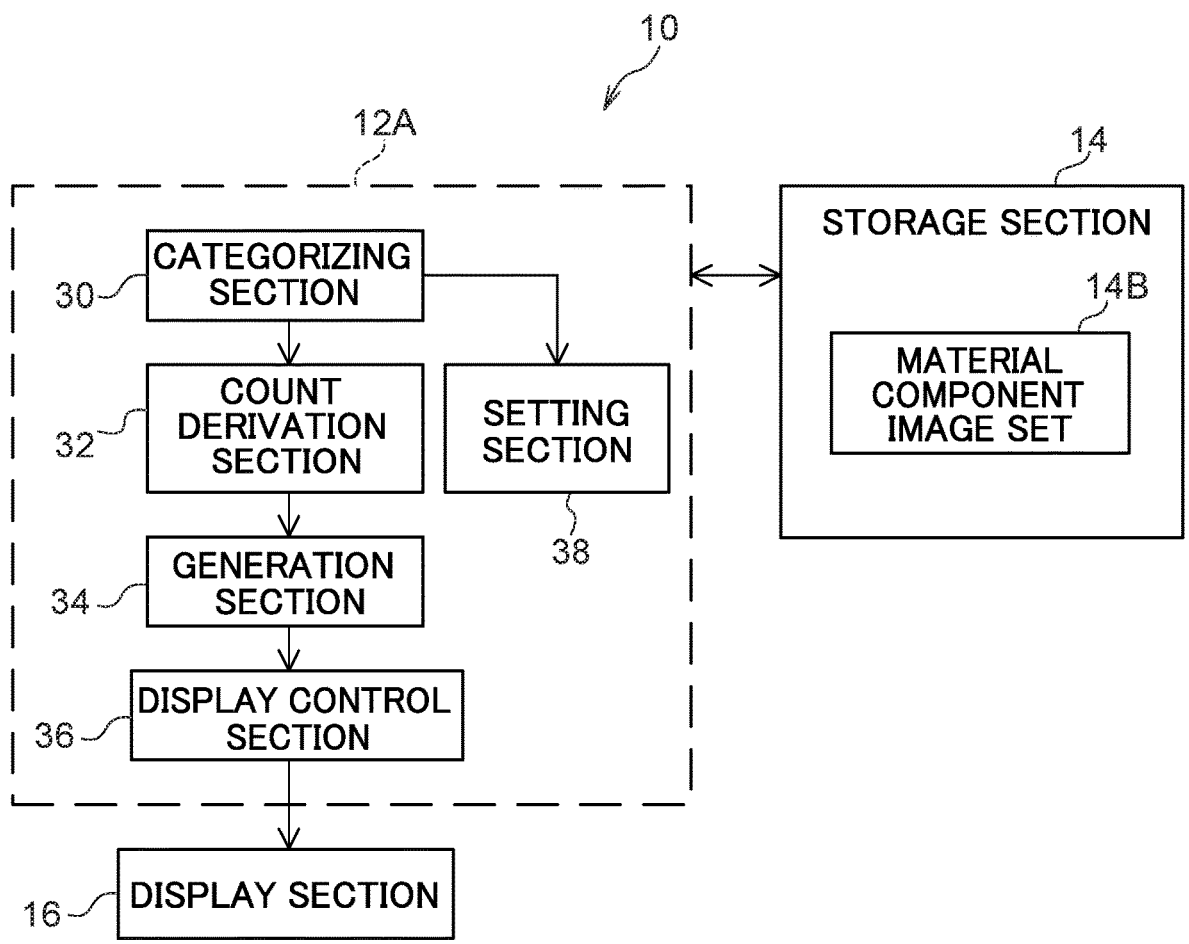
FIG. 4 is a block diagram illustrating an example of a functional configuration of an information processing device according to an exemplary embodiment.

The CPU 12A of the information processing device 10 according to the present exemplary embodiment functions as the respective sections illustrated in FIG. 4 by writing the image processing program 14A stored in the storage section 14 into the RAM 12C and executing the image processing program 14A.

FIG. 4 is a block diagram illustrating an example of a functional configuration of the information processing device 10 according to the present exemplary embodiment.

As illustrated in FIG. 4, the CPU 12A of the information processing device 10 according to the present exemplary embodiment functions as a categorizing section 30, a count derivation section 32, a generation section 34, a display control section 36, and a setting section 38. Note that the display control section 36 is an example of a control section.

The categorizing section 30 according to the present exemplary embodiment takes plural images (for example 300 or 1000 images) obtained by the camera 74 imaging the sample fluid flowing through the flow cell 40, and from the plural images, extracts material component images of the plural types of material component contained in a sample fluid. The categorizing section 30 then categorizes the extracted material component images into predetermined categories (for example by the type, size, or shape of the material components, or by the presence or absence of a nucleus therein). The material component images categorized into the predetermined categories by the categorizing section 30 are stored in the storage section 14 as a material component image set 14B for each sample. Note that various known methods may be employed as the method for identifying material components in the images, such as a method employing machine learning or a method employing pattern matching. The material component image set 14B is also referred to as the material component images 14B when referring to individual material component images within the material component image set 14B.

The count derivation section 32 according to the present exemplary embodiment derives counts by category for material components contained in the sample fluid, and counts of material components present per standard visual field, based on the number of material component images categorized into each category by the categorizing section 30. Specifically, for each of the predetermined categories, the count derivation section 32 uses a calibration curve to convert the number of material component images acquired from a single sample measurement into counts per unit liquid volume of the sample fluid. Counts per standard visual field are then derived from the thus converted counts per unit liquid volume by using a predetermined correction coefficient for each visual field. Note that reference to calibration curves also encompasses functions, and data expressing correlations such as conversion coefficients, conversion tables, etc.

Figure 5:
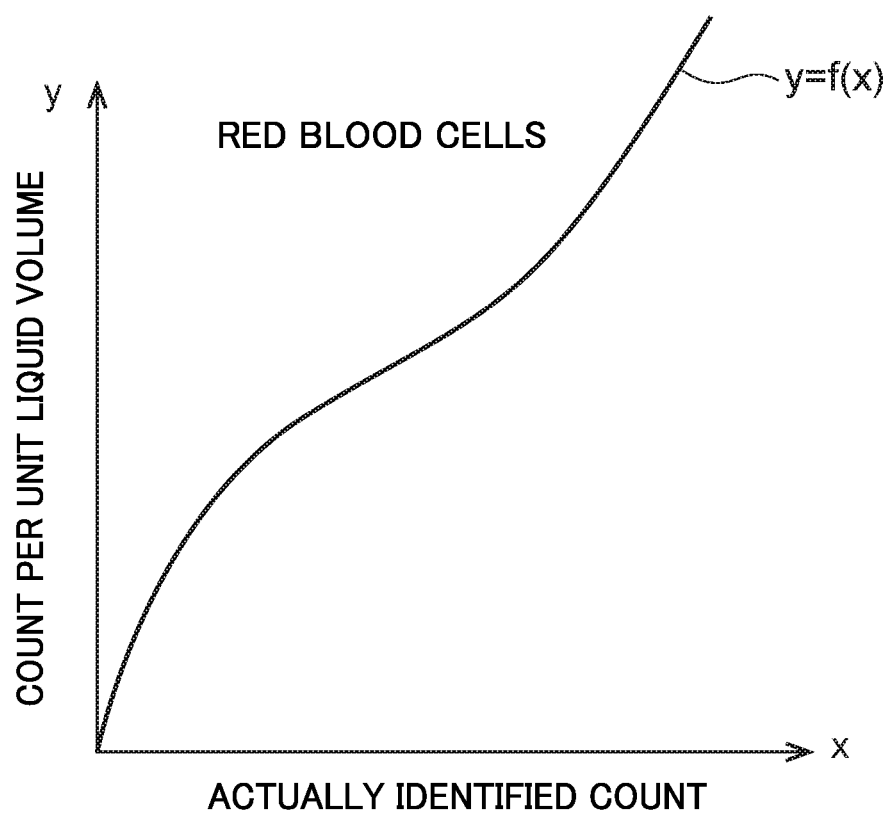
FIG. 5 is a graph illustrating one example of a calibration curve as employed for each material component according to an exemplary embodiment.

FIG. 5 is a graph illustrating an example of a calibration curve as employed for each material component according to the present exemplary embodiment.

In FIG. 5, the horizontal axis represents the count of material components actually identified in a single sample measurement, and the vertical axis represents the count of material components per unit liquid volume of the sample fluid. Note that a calibration curve for red blood cells is illustrated as a representative example in the present exemplary embodiment.

The camera 74 is not actually capable of imaging all of the sample fluid when the sample fluid flows through the flow cell 40. A sample amount imageable by the camera 74 is accordingly ascertained. The imageable sample amount is determined using a control liquid containing standard particles. For example, if 500 standard particles are captured in plural images imaged by the camera 74 when 1 µl of a control liquid containing 2000 standard particles per µl flows through the flow cell 40, then the sample amount imageable by this measurement system is determined to be 0.25 µl, or in other words a sample amount corresponding to 25% of the sample amount that flowed.

The differing size, shape, composition, outline definition, and the like for each type of material component results in differences in the ease (rate) of flowing through an imaging area of the camera 74, the ease with which the camera 74 can be focused thereon, and the ease with which the material components can be identified in the captured images. There is accordingly a difference by category in the rate with which the material components are captured as extracted images.

In consideration of the above points, a calibration curve expressed by a function y=f(x) is created so as to reflect the imageable sample amount and the capture rate for each category. The calibration curve illustrated in FIG. 5 is a graph representing a relationship between red blood cell counts (measured values) actually identified in plural images captured by the camera 74, and red blood cell counts contained per unit liquid volume. The graph expressing this calibration curve is created based on actual measurement results obtained and on accurate count data for the corresponding material component as measured using another method. In addition to red blood cells, such calibration curves are also created for the other categories, namely white blood cells, epithelial cells, casts, bacteria, and the like. Note that data of the calibration curves created is stored in advance in the storage section 14 for reference by the count derivation section 32. The calibration curves are used to acquire counts of material components contained per unit liquid volume (for example per 1 μl) of the sample from the number of material component images.

Predetermined correction coefficients for respective visual fields are then used to derive the counts per standard visual field for material components of each category from the counts per unit liquid volume obtained for each category. Here, a "visual field" refers to the range that can be seen at any one time through a microscope using, for example, a high power field (HPF: strong magnification ratio equivalent to 400×) or a low power field (LPF: weak magnification ratio equivalent to 100×) for microscopic examination (standard method). The correction coefficient is decided based on the surface area of the standard visual field, as well as the placement of the sample at the imaging location, the concentration multiplier, and the urine sample volume. In the present exemplary embodiment, α is the correction coefficient for HPF, and β is the correction coefficient for LPF. The correction coefficient α is set based on the relationship between the imaging range captured by the camera 74 and that for an HPF, and the correction coefficient β is set based on the relationship between the imaging range captured by the camera 74 and that for an LPF. The correction coefficients α, β are stored in advance in the storage section 14. Note that $N_\alpha$ and $N_\beta$ are computed using the following Equations (1) and (2), wherein $N_\alpha$ is a count for an HPF, $N_\beta$ is a count for an LPF, and $N_u$ is a count per unit liquid volume. Note that $N_u$ is different for each category.

$$N_\alpha = \alpha \times N_u \qquad \text{Equation (1)}$$

$$N_\beta = \beta \times N_u \qquad \text{Equation (2)}$$

Explanation follows regarding specific examples in which HPF and LPF counts are derived for red blood cells, white blood cells, and bacteria. For example, if the actual red blood cell count measured is 10, then the calibration curve for red blood cells is employed to convert this count into a count of 15/μl. Then Equation (1) and Equation (2) are used to derive counts of (α×15)/HPF and (β×15)/LPF. Moreover, if the actual white blood cell count measured is 15, the calibration curve for white blood cells is employed to convert this count into a count of 20/μl, and then Equation (1) and Equation (2) are used to derive counts of (α×20)/HPF and (β×20)/LPF. Moreover, if the actual bacteria count measured is 20, the calibration curve for bacteria is employed to convert to this count into a count of 400/μl, and then Equation (1) and Equation (2) are used to derive counts of (α×400)/HPF and (β×400)/LPF. Note that the standard visual field may also employ a visual field with a magnification ratio other than that of HPF or LPF, and a user may set a desired standard visual field size.

Next, the generation section 34 according to the present exemplary embodiment generates a single all-component image in which plural material component images corresponding to the counts for each category per standard visual field, as derived by the count derivation section 32, are randomly arranged in an area corresponding to the standard visual field. When this is performed, the plural material component images are preferably arranged such that they do not overlap each other. The background color often differs between each of these plural material component images, and this could result in an unnatural looking all-component image. In order to reduce any such unnaturalness in the all-component image the plural material component images are preferably adjusted to a uniform color tone. This color tone may, for example, be set as any one out of an average value, a maximum value, or a minimum value of pixel values representing the background colors of the plural material component images. Moreover, images in which the material component images are in focus are preferably employed therefor. The all-component image is a pseudo image generated by arranging material component images, which have been obtained by categorizing the images extracted from the captured images by material component, according to the respective quantities thereof contained in the sample fluid. For example, in a case in which the standard visual field is set to HPF (equivalent to 400×), the generated all-component image is an image equivalent to an image with a 400' magnification ratio as observed in a microscopic examination (standard method).

Figure 6:
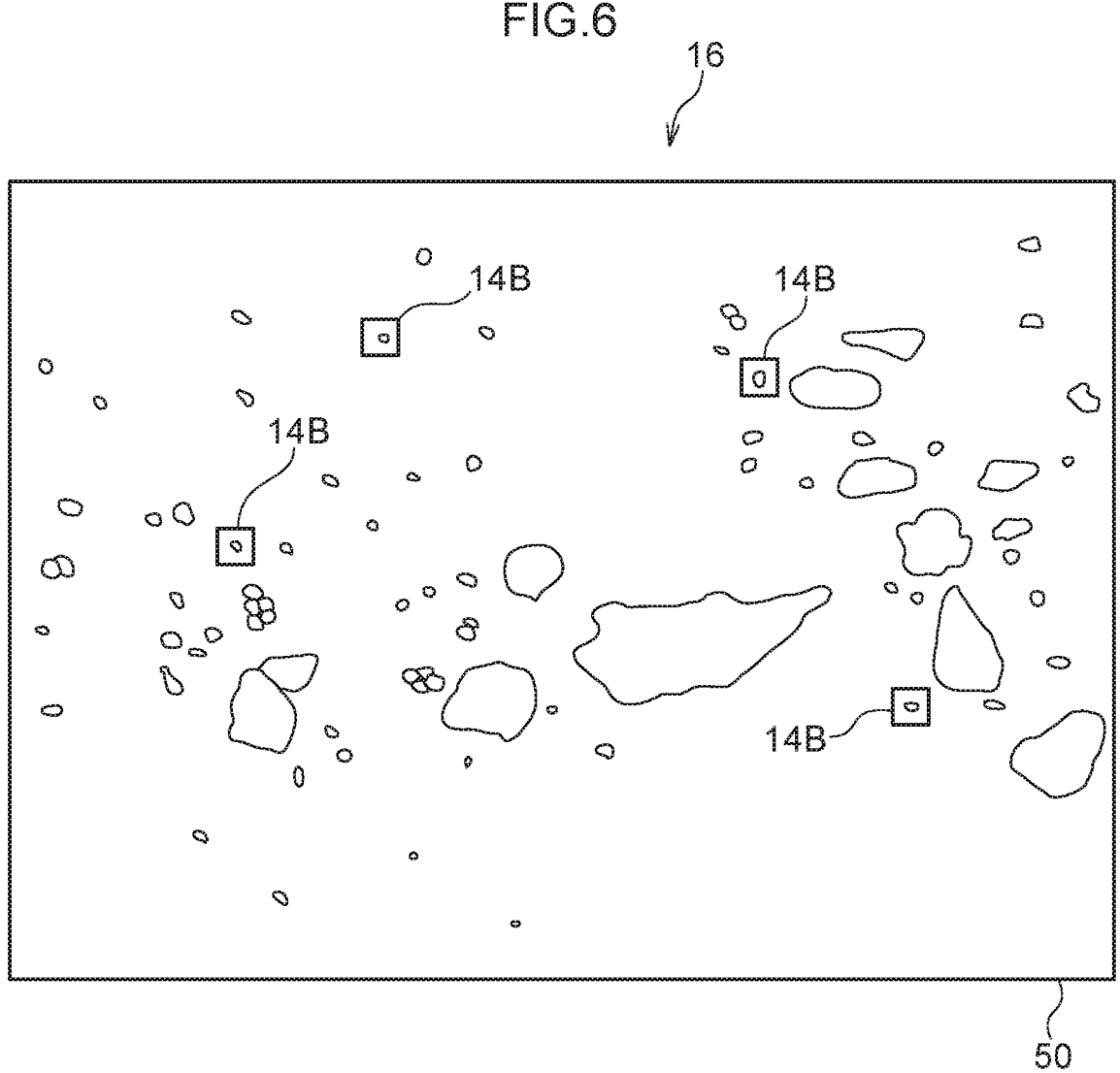
FIG. 6 is a face-on view illustrating an example of an all-component image screen according to an exemplary embodiment.

Next, as an example, the display control section 36 according to the present exemplary embodiment controls so as to display the all-component image generated by the generation section 34, as illustrated in FIG. 6.

FIG. 6 is a face-on view illustrating an example of an all-component image screen 50 according to the present exemplary embodiment.

As illustrated in FIG. 6, the all-component image screen 50 according to the present exemplary embodiment displays the all-component image in which the material component images 14B are arranged according to the counts per category, as described above. The all-component image screen 50 is displayed on the display section 16. Although an example is described above in which the all-component image is created for the counts contained in a standard visual field, the all-component image may be created for a desired setting for the liquid volume and image size based on the respective counts contained per unit liquid volume of the sample, or the all-component image may be created for a unit liquid volume based thereon. Moreover, a display mode may be selected or changed by a user. In cases in which an all-component image is created for a unit liquid volume, the user is able to set or change the unit liquid volume to the desired unit liquid volume.

The display control section 36 may perform control so as to selectively display only specific material component images contained in the all-component image. Such control of display may, for example, be performed by selecting an item button corresponding to the specific material component image from an item button array 51, illustrated in FIG. 7.

Figure 7:
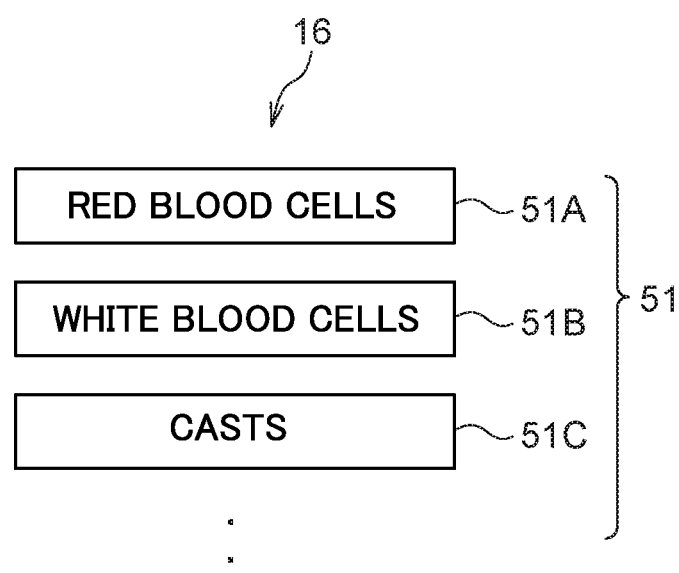
FIG. 7 is a diagram illustrating an example of an item button array according to an exemplary embodiment.

FIG. 7 is a diagram illustrating an example of the item button array 51 according to the present exemplary embodiment.

As illustrated in FIG. 7, the item button array 51 according to the present exemplary embodiment is displayed on the display section 16 together with the all-component image of the all-component image screen 50. The item button array 51 includes item buttons 51A, 51B, 51C, etc. corresponding to each of the material components.

As an example, the item button array 51 illustrated in FIG. 7 includes an item button 51A corresponding to red blood cells, an item button 51B corresponding to white blood cells, an item button 51C corresponding to casts, and so on. For example, when the item button 51A has been selected, only images of red blood cells are selectively displayed on the all-component image screen 50 illustrated in FIG. 6, and the other material components are not displayed. Similarly, when the item button 51B has been selected, images of only white blood cells are selectively displayed on the all-component image screen 50 illustrated in FIG. 6, and the other material components are not displayed. Moreover, configuration may be made such that when plural item buttons in the item button array 51 have been selected, the plural selected material components are displayed, and other material components are not displayed.

The display control section 36 may also be configured to perform control to change a display settings mode in which, for example, the item button array 51 illustrated in FIG. 7 is operated to select material components that are not of interest (components not of interest) from among the plural material component images contained in the all-component image, so that the material component images that are components selected as not of interest are not displayed. Alternatively, the display control section 36 may be configured to perform control such that a number of images exceeding an upper limit value are not displayed for material component images of images that are not of interest. As another example, material component images corresponding to item buttons that were not selected from the item button array 51 illustrated in FIG. 7 may be determined to be not of interest. Note that the upper limit value is set in advance for each of the material components. For example, in a case in which an upper limit value of 30 has been set for material component images representing white blood cells, then in a case in which 40 material component images representing white blood cells would be displayed in the all-component image if white blood cells have not been selected as not being of interest, the display control section 36 may perform a control such that up to 30 of the material component images representing white blood cells are displayed but the $31^{st}$ image onward thereof are not displayed, or such that none of the material component images representing white blood cells are displayed, when white blood cells are not of interest. This enables a reduction in the number of material component images that are not of interest which are displayed, enabling greater emphasis to be placed on the material component images that are of interest.

Next, the setting section 38 according to the present exemplary embodiment sets an upper limit for the number of material component images for each category to be stored in the storage section 14 from out of the material component images categorized by the categorizing section 30. Note that this upper limit number may be modified as appropriate. For example configuration may be made such that even if 100 instances of a particular material component have been counted, the number stored as images is 30. If all the material component images for all the material components that had been counted were to be stored then the storage capacity of the storage section 14 might rapidly become insufficient therefor. It is thus desirable to store only the required number of the required material component images in each sample. Although such an approach could potentially lead to there being insufficient material component images to generate the all-component image, the ability to adjust the number of images stored by category in this manner would enable such issues to be addressed by measures such as increasing the number of images to be stored for material components that are of interest.

In cases in which the number of material component images for each category that are to be disposed as part of the all-component image exceeds the upper limit for the number of images stored in the storage section 14, the generation section 34 according to the present exemplary embodiment may be configured so as to duplicate material component images from out of the material component images stored in the storage section 14 so as to acquire material component images to make up the excess amount. Namely, in cases in which there are insufficient material component images, duplicates of the material component images stored in the storage section 14 may be employed. Such cases include not only configurations in which simple duplication is performed, but also configurations in which processing is performed to rotate the orientation of such images, or enlarge or shrink such images.

Figure 8:
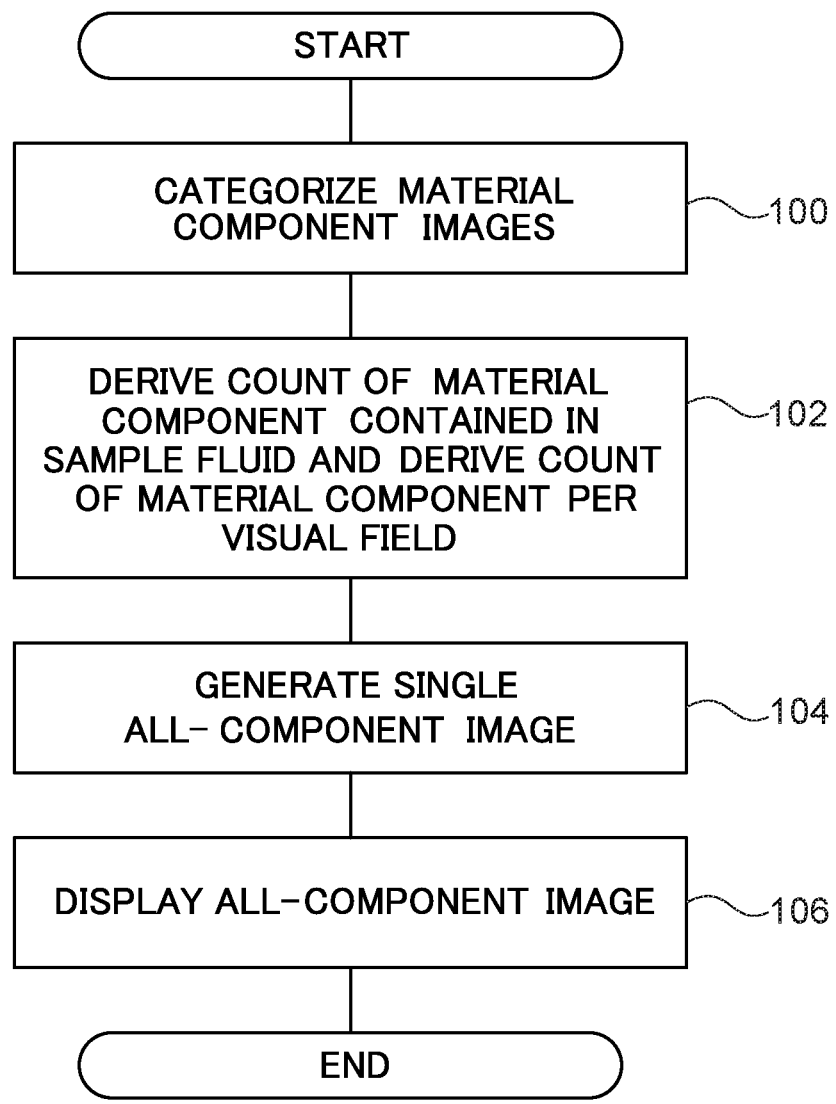
FIG. 8 is a flowchart illustrating an example of a flow of processing of an image processing program according to an exemplary embodiment.

Explanation follows regarding operation of the information processing device 10 according to the present exemplary embodiment, with reference to FIG. 8.

FIG. 8 is a flowchart illustrating an example of a flow of processing by the image processing program 14A according to the present exemplary embodiment.

First, each of the following steps is executed when the information processing device 10 receives an instruction to start all-component image display processing.

At step 100 in FIG. 8, the categorizing section 30 extracts material component images identified as each of the respective plural types of material components from the plural images acquired by imaging the sample fluid flowing through the flow cell 40 using the camera 74. The material component images thus extracted are then categorized by category (for example, by material component type). The material component images that have been categorized by category by the categorizing section 30 are then stored in the storage section 14 as the material component image set 14B.

At step 102, the count derivation section 32 derives for each category a count for the material components for a standard visual field or a count for the material components per unit liquid volume contained in the sample fluid, based on the numbers of material component images in each category as categorized at step 100. Specifically, as an example, the number of material component images are converted into the counts per unit liquid volume by employing a calibration curve such as that illustrated in FIG. 5. For example, the Equation (1) and Equation (2) described above are employed to derive the counts for a standard visual field from the converted counts per unit liquid volume.

At step 104, the generation section 34 generates the all-component image by arranging the plural material component images so as not to overlap with each other, in numbers according to the counts per category derived at step 102.

At step 106, as an example the display control section 36 performs control to display the all-component image generated at step 104 as illustrated in FIG. 6, and the sequence of processing by the image processing program 14A is then ended.

Figure 9:
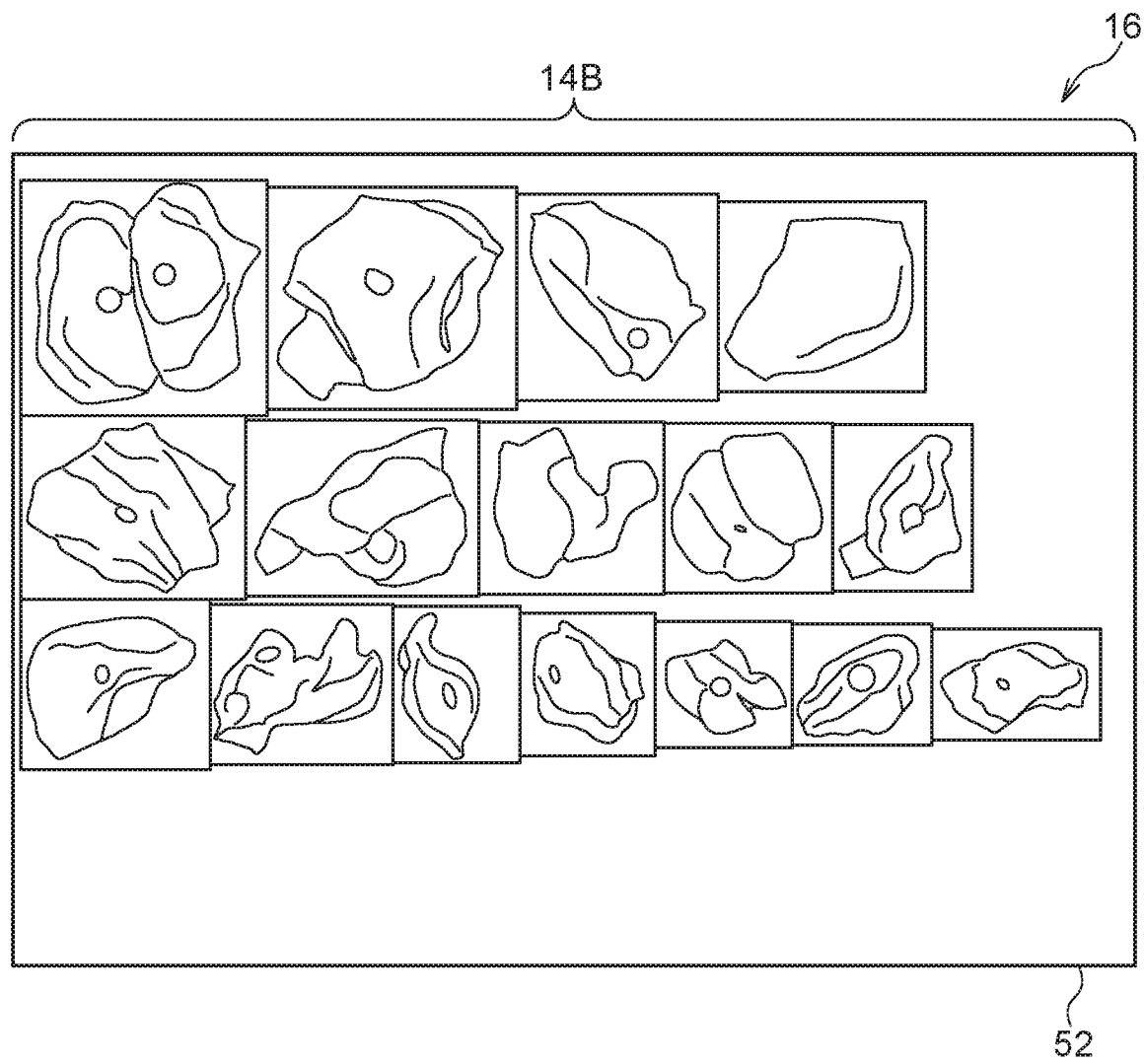
FIG. 9 is a face-on view illustrating an example of a material component image list screen according to an exemplary embodiment.

Next, explanation follows regarding an example of a material component image list screen and a measurement result screen according to the present exemplary embodiment, with reference to FIG. 9 and FIG. 10.

FIG. 9 is a face-on view illustrating an example of a material component image list screen 52 according to the present exemplary embodiment.

As illustrated in FIG. 9, the material component image list screen 52 according to the present exemplary embodiment is a display of the material component images 14B by category. The material component image list screen 52 is displayed on the display section 16.

Namely, as described above, the material component images categorized into each category by the categorizing section 30 are stored in the storage section 14 as the material component image set 14B. For example, when an operator wants to check the material component images for red blood cells, the operator selects a predetermined operation button (not illustrated in the drawings) to instruct the material component images 14B for red blood cells to be read from the storage section 14 and displayed as the material component image list screen 52. Note that the material component image list screen 52 is similarly displayable for material components other than red blood cells, for example white blood cells and bacteria.

FIG. 10 is a face-on view illustrating an example of a measurement result screen 54 according to the present exemplary embodiment.

As illustrated in FIG. 10, the measurement result screen 54 according to the present exemplary embodiment is a display of a measurement results table, together with an operation button 54A for displaying an all-component image. The measurement results shown include a contained amount or count for a standard visual field (HPF) as computed by the count derivation section 32, a contained amount or count per unit liquid volume as computed thereby, and qualitative indices for contained amounts.

Main items among the items illustrated in FIG. 10 include, for example, RBC (red blood cells), WBC (white blood cells), NSE (non-squamous epithelial cells), SQEC (squamous epithelial cells), NHC (non-hyaline casts), and BACT (bacteria). Moreover, CRYS (crystals), YST (yeast), HYST (hyaline casts), MUCS (mucus), SPRM (spermatozoa), and WBCC (white blood cell clumps) are also illustrated.

The operation button 54A of the present exemplary embodiment is a button labeled "VIEW ALL-COMPONENT IMAGE". When the operator selects the operation button 54A, as an example, the all-component image screen 50 illustrated in FIG. 6 described above is displayed.

FIG. 11 is a diagram to explain a process for generating the all-component image according to the present exemplary embodiment.

As illustrated at the top of FIG. 11, plural of the material component images 14B are arranged according to the counts for each category so as to obtain an image 56.

As illustrated at the bottom of FIG. 11, the color tones of background colors and the like of each of the material component images 14B are adjusted in the image 56 so as to generate a single natural-looking all-component image 58. The red blood cells, white blood cells, bacteria, casts, etc. serving as examples of material components are included in the all-component image 58 in numbers thereof similar to how they would appear if observed through a microscope.

In the present exemplary embodiment, counts for material components imaged by the camera are derived per standard visual field for each category. This enables an all-component image with a feel similar to that of a microscope observation to be observed, even in cases in which image capture is performed using a flow method. Moreover, the ability to observe a screen displaying plural categorized elements imaged by the camera facilitates common properties and shapes (swollen, shriveled, etc.) to be ascertained in the plural material components, which would be more difficult to spot in individual extracted images.

Explanation has been given regarding an example of an information processing device according to an exemplary embodiment. The present exemplary embodiment may be provided in the format of a program configured to cause a computer to execute the functions with which the respective sections of the information processing device are equipped. The present exemplary embodiment may be provided in the format of a computer-readable storage medium stored with such a program.

Configurations of the information processing device described in the above exemplary embodiment are moreover merely examples thereof, and may be modified according to circumstances within a range not departing from the spirit thereof.

The processing flow of the program described in the above exemplary embodiment is moreover also merely an example thereof, and steps not required may be omitted, new steps may be added, or the processing sequence may be altered within a range not departing from the spirit thereof.

Although explanation in the above exemplary embodiment is regarding a case in which execution of the program results in the processing of the present exemplary embodiment being implemented by a software configuration employing a computer, there is no limitation thereto. For example, an exemplary embodiment may be implemented by a hardware configuration, or by a combination of a hardware configuration and a software configuration.

What is claimed is:

1. An information processing device comprising:
a memory; and
a processor coupled to the memory;
the processor being configured to
extract a material component image identified as a material component, from a plurality of images obtained by imaging a sample fluid containing a plurality of types of material components and flowing through a flow cell, and categorize the extracted material component image by predetermined category;
compute a count of the material component per standard visual field, or compute a count per unit liquid volume of the material component contained in the sample fluid, for each predetermined category based on a number of categorized material component images; and
generate an all-component image in which a plurality of the material component images are arranged according to the counts that have been counted for each predetermined category.

2. The information processing device of claim 1, wherein the processor is configured to use a predetermined calibration curve for each predetermined category to convert a number of the material component images into a resulting count per unit liquid volume of the sample fluid, and to use a predetermined correction coefficient for each visual field to compute a count per standard visual field from the resulting count per unit liquid volume.

3. The information processing device of claim 1, wherein the processor is configured to arrange the plurality of material component images so as not to overlap with each other.

4. The information processing device of claim 3, wherein the processor is configured to adjust a background color of each of the plurality of material component images to a uniform color tone.

5. The information processing device of claim 4, wherein the color tone is determined by one out of an average value, a maximum value, or a minimum value of pixel values representing the background color in each of the plurality of material component images.

6. The information processing device of claim 1, wherein:
the processor is further configured to display the all-component image that has been generated; and
the processor is configured to selectively display only a specific material component image included in the all-component image.

7. The information processing device of claim 6, wherein the processor is configured to not display any material component image selected among the plurality of material component images included in the all-component image, or to not display a number of images exceeding an upper limit value for material component images selected.

8. The information processing device of claim 1, further comprising a storage section storing categorized material component images, wherein the processor is further configured to set an upper limit for each of the categories for a number of the material component images, among the material component images that have been categorized, to be stored in the storage section.

9. The information processing device of claim 8, wherein the processor is configured to duplicate material component images stored in the storage section in a case in which a number of material component images for each predetermined category to be arranged as part of the all-component image exceeds the upper limit, so as to acquire material component images for the amount by which the upper limit is exceeded.

10. An information processing method comprising:
extracting a material component image identified as a material component from a plurality of images obtained by imaging a sample fluid containing a plurality of types of material components and flowing through a flow cell, and categorizing the extracted material component image by predetermined category;
computing a count of the material component per standard visual field, or computing a count per unit liquid volume of the material component contained in the sample fluid, for each predetermined category based on a number of categorized material component images; and
generating an all-component image in which a plurality of the material component images are arranged according to the counts that have been computed for each predetermined category.

11. A measurement system comprising:
a flow cell configured to allow a sheath fluid and a sample fluid that contains a plurality of types of material components to flow through;
an imaging section configured to image the sample fluid flowing through the flow cell; and
the information processing device of claim 1 input with a plurality of images obtained by imaging with the imaging section.

12. A non-transitory storage medium storing a program for causing a computer to execute processing, the processing comprising:
extracting a material component image identified as a material component from a plurality of images obtained by imaging a sample fluid containing a plurality of types of material components and flowing through a flow cell, and categorizing the extracted material component image by predetermined category;
computing a count of the material component per standard visual field, or computing a count per unit liquid volume of the material component contained in the sample fluid, for each predetermined category based on a number of categorized material component images; and
generating an all-component image in which a plurality of the material component images are arranged according to the counts that have been computed for each predetermined category.

13. The information processing device of claim 1, wherein the processor is configured to randomly arrange the plurality of material component images.

14. The information processing device of claim 1, wherein the processor is configured to generate the all component image in which a plurality of the material component images are arranged in an area corresponding to the standard visual field or corresponding to a liquid volume of a sample according to the counts that have been computed for each predetermined category.

* * * * *